United States Patent [19]

Stokes et al.

[11] Patent Number: 5,300,107
[45] Date of Patent: Apr. 5, 1994

[54] UNIVERSAL TINED MYOCARDIAL PACING LEAD

[75] Inventors: Kenneth B. Stokes, Brooklyn Park; Keith J. Proctor, Lino Lakes; Tommy D. Bennett, Shoreview; Rick D. McVenes, Ham Lake, all of Minn.

[73] Assignee: Medtronic, Inc., Minneapolis, Minn.

[21] Appl. No.: 964,737

[22] Filed: Oct. 22, 1992

[51] Int. Cl.⁵ ............................................. A61N 1/362
[52] U.S. Cl. ................................................... 607/126
[58] Field of Search ................ 128/642; 607/122, 126, 607/128, 116; 604/105, 106, 107

[56] References Cited

U.S. PATENT DOCUMENTS

| | | |
|---|---|---|
| 3,902,501 | 9/1975 | Citron et al. |
| 4,269,198 | 5/1981 | Stokes . |
| 4,407,303 | 10/1983 | Akerström ..................... 607/126 |
| 4,585,013 | 4/1986 | Harris . |
| 4,590,949 | 5/1986 | Pohndorf . |
| 4,658,835 | 4/1987 | Pohndorf . |
| 4,716,888 | 1/1988 | Wesner . |
| 4,722,353 | 2/1988 | Sluetz . |
| 4,796,643 | 1/1989 | Nakazawa . |

Primary Examiner—Lee S. Cohen
Assistant Examiner—Jeffrey R. Jastrzab
Attorney, Agent, or Firm—Harold R. Patton

[57] ABSTRACT

A myocardial pacing lead includes two sets of at least two tines placed to oppose each other. The lead is pressed against the epicardium and is rotated until a rough porous tip abrades the epicardium and allows the tip and the first row of tines to penetrate the myocardium. Excessive penetration and lead migration is prevented by the second row of tines which is mounted backward and just proximal from the first row of tines. The first row of tines anchor on the inside surface of the epicardium which prevents dislodgment. Dacron pads on the second row of tines assures chronic fixation by adhering to the outer surface of the patient's epicardium.

21 Claims, 3 Drawing Sheets

UNIVERSAL TINED MYOCARDIAL PACING LEAD

FIELD OF THE INVENTION

The present invention relates to a medical electrode lead and more particularly to a myocardial pacing lead employing a tip configuration to prevent excessive penetration into a patient's myocardium.

Electrical stimulation of the body for medical purposes is well known in the prior art. An example of a device for this purpose is the well known cardiac pacemaker. In general, pacemakers employ an electrode that is maintained in contact with a patient's heart muscle, through which electrical stimulation of the heart muscle is achieved. Such pacemakers commonly employ a flexible conductive lead that connects a remotely positioned and implanted power source to the electrode tip. The lead is typically routed to achieve either passive or active fixation to the heart muscle. Active fixation means such as corkscrews or hooks have been used to maintain the electrode tip in contact with the heart muscle. Alternatively, passive fixation means have been employed to temporarily hold the electrode tip in contact with the heart muscle until sufficient tissue ingrowth has occurred about the electrode tip to hold it in place. Such a passive device is disclosed in Citron et al. U.S. Pat. No. 3,902,501, who provide a plurality of pliant tines extending from the electrode adjacent the tip and forming an acute angle with respect to the electrode body. The tines cooperate with the trabeculae in the heart muscle to hold the electrode tip in position until such time as natural fixation has occurred.

Interactions between the lead and the patient's body can vitiate the desired effects of the stimulation. For example, biologic reactions encourage fibrosis. Furthermore, trauma results in inflammation of the tissue to be stimulated. Other interactions between the lead and body, while not directly affecting the response of the tissue to the stimulation energy, can result in the occurrence of undesirable events. The placement of a lead may compound certain events such as irritability.

Efforts have been made to ameliorate the undesirable consequences of interactions between lead and body. For example, leads have been configured to reduce mechanical trauma and the response of the irritable tissue during lead placement. Materials have been selected for the lead body and electrodes to minimize fibrosis. However, lead configuration must take into account other factors such as the ease of placement, maintenance of the desired electrode position and the reliability of the lead over extended periods of time.

Undesirable interactions between lead and body are a particular problem in the context of a myocardial lead employing a penetrating electrode, especially in the area of pediatrics. Unlike the electrodes of most endocardial leads, penetrating myocardial electrodes are intended to function by insertion into the tissue, rather than by placement against the tissue. As such, the basic mode of operation of these electrodes requires some small amount of tissue damage to accompany attachment of the electrode. The greater the reaction of the heart tissue to this injury, the more likely it is that subsequent problems of increased threshold, fibrosis or irritability will rise. This is particularly true in the area of pediatrics. Thus, there is a need for a low threshold, high pacing impedance myocardial lead suitable for pediatrics.

SUMMARY OF THE INVENTION

The present invention provides a body implantable high impedance, low threshold, tined, myocardial lead for the delivery of stimulation energy suitable for use in adult and pediatric applications. In one embodiment, a high impedance, low threshold, steroid eluting lead with a rough porous tip, includes two sets of at least two tines placed to oppose each other. The lead (with stylet) is pressed against the epicardium and is rotated. The rough porous tip abrades the epicardium and allows the tip and the first row of tines to penetrate the myocardium. Excessive penetration and lead migration is prevented by the second row of tines which is mounted backward and just proximal from the first row of tines. The first row of tines anchor on the inside surface of the epicardium thereby preventing dislodgment. Withdrawal of the stylet allows the lead to assume any existent preformed shape. Dacron pads on the second row of tines assures chronic fixation by adhering to the outer surface of the patient's epicardium. Controlling the depth of the first row of tines allows for chronic removal by counter traction without tearing or otherwise damaging the heart.

Another embodiment allows a similar lead to be implanted transvenously to provide positive or passive fixation. Positive fixation is achieved by applying slight pressure and rotating the lead until the tip pops into the endocardium as far as the first row of tines will allow. Passive fixation is achieved by simply placing the lead as any other prior art tined lead is placed.

Thus, the inventive lead can achieve the implant characteristics of an epicardial lead, a transvenous tined lead or a transvenous active fixation lead.

DETAILED DESCRIPTION OF THE INVENTION

Figure 1:
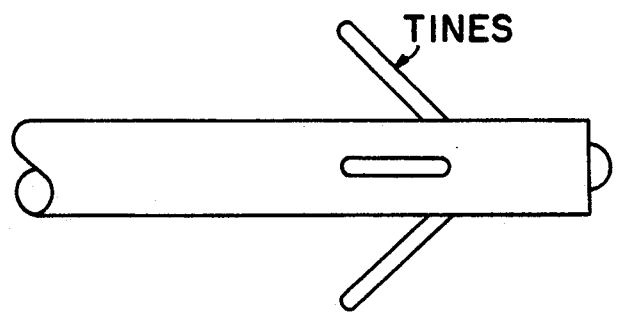
FIG. 1 illustrates a side view of the distal end portion of a tined lead with a single row of tines as is already known in the prior art.

Referring now to FIG. 1, there is illustrated a body implantable tined lead already known in the prior art. Tined leads such as this one are passively attached to heart muscle without penetrating the myocardium. An example of such a lead is disclosed in U.S. Pat. No.

Figure 2:
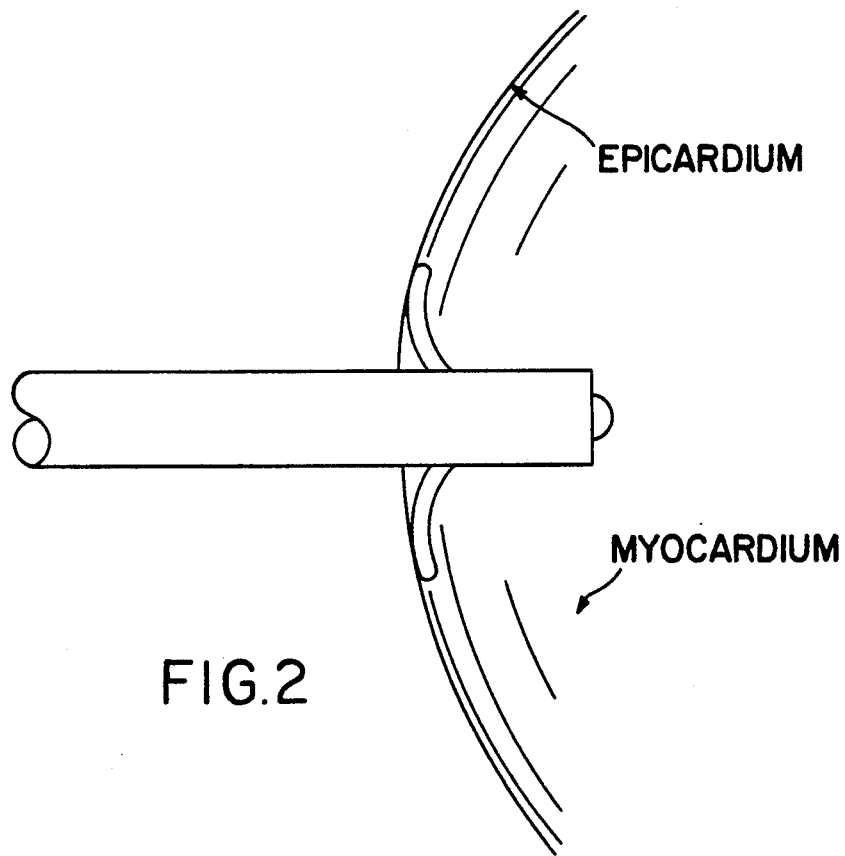
FIG. 2 illustrates active fixation of the distal end portion of the prior art tined lead depicted in FIG. 1 to a myocardium.

4,269,198 issued to Stokes. Active fixation of a lead such as the lead invented by Stokes is illustrated in FIG. 2. This type of application, with a single row of tines, has no means for preventing migration of the lead within the myocardium. Additionally, no means exist in such an application for controlling the depth of the lead into the myocardium for procuring active fixation. Controlling the depth of active fixation into the myocardium and preventing migration of the lead tip subsequent to lead fixation become even more significant implant concerns in the area of pediatrics where patient organs are smaller and more fragile than fully developed adult organs.

Figure 3:
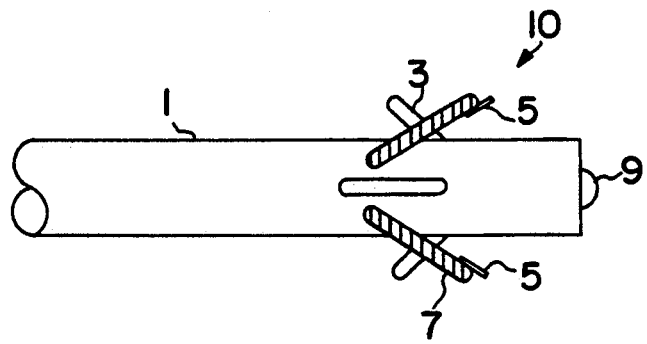
FIG. 3 illustrates a side view of the distal end portion of a preferred embodiment of the present invention.

Moving now to FIG. 3, there is illustrated a side view of the distal end of a preferred embodiment of the present inventive lead capable of both controlling the depth of active fixation into a myocardium and preventing migration of the lead tip, effective in adult and pediatric applications. The proximal end, not shown, is coupled to an electrical connector such as those known in the prior art. The preferred embodiment, illustrated in FIG. 3, also comprises an electrical conductor, not shown, within the insulating sheath 1. A tip electrode 9, preferably having a surface area less than 4.0 mm$^2$, is provided at the distal end of the lead assembly 10 in a manner described in pending continuation application Ser. No. 07/887,560 for HIGH IMPEDANCE, LOW POLARIZATION, LOW THRESHOLD MINIATURE STEROID ELUTING PACING LEAD ELECTRODES which is a continuation of continuation application Ser. No. 07/759,191 which is a continuation of original parent application Ser. No. 07/539,102, all of which have been assigned to Medtronic, Inc. Proximal to electrode 9, is a row of standard tines 3, identical to those shown in FIG. 1 and already known in the prior art, formed of a pliant material which is generally inert to body fluids; silicone rubber or polyurethane, for example. The tines 3, are attached to the body member 1, in the traditional manner known in the prior art. The tines 3, may take any acute angle with the proximal end of body member 1, their purpose being to anchor to the inside wall of the epicardium, thereby preventing accidental dislodgment and maintaining the tip 9, in electrical contact with the myocardium. A second row of backward mounted tines 7, proximal the first row of tines 3, is located between the proximal end of lead assembly 10 and the first row of tines 3. The tines 7, in the second row must be longer than tines 3, in the first row to allow implantation into the myocardium. Tines 7 on the lead body 1 form an acute with body member 1 which is in opposition to the acute angle formed by tines 3 and body, member 1. Additionally, tines 7 have "DACRON" (synthetic fiber) pads 5 attached to their free floating ends for assuring chronic fixation of tines 7 to the outside wall of the epicardium.

Figure 4:
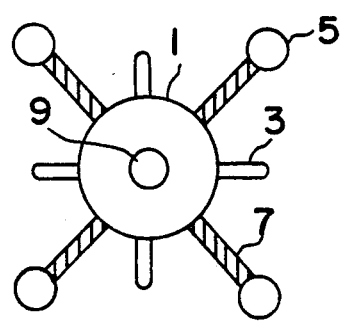
FIG. 4 illustrates an end view of the distal end portion of a preferred embodiment of the present invention.

Referring now to FIG. 4, there is illustrated an end view of the preferred embodiment of the present inventive myocardial lead of FIG. 3 as seen from the distal end containing tip electrode 9. Although four tines 3 are depicted in the first row, and four tines 7 are depicted in the second row, any number of tines may be used, two or more being adequate in most situations. Furthermore, it is preferable to have the tines 3 in the first row alternately and evenly spaced with the tines 7 in the second row as indicated in FIG. 4, although such spacing and tine placement is not required for the present invention t function properly.

Figure 5:
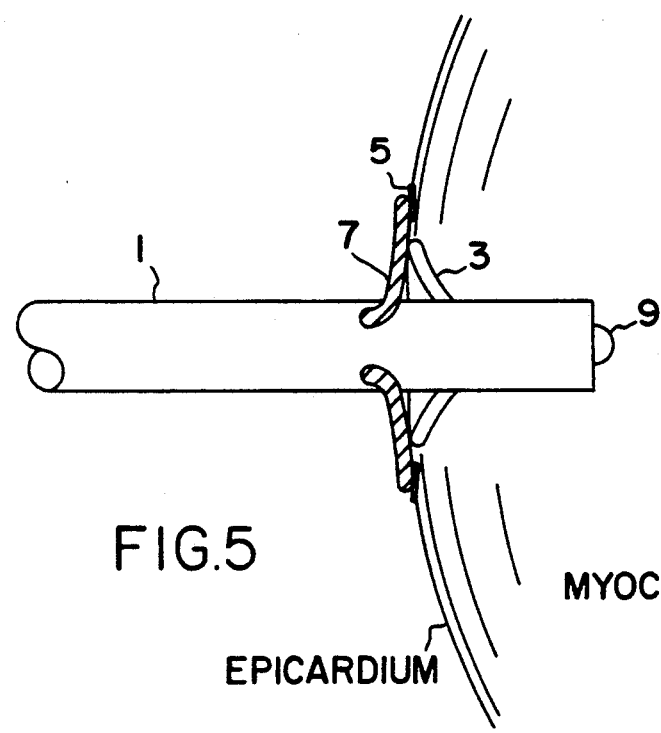
FIG. 5 illustrates active fixation of the distal end portion of a preferred embodiment of the present invention to a myocardium.

FIG. 5 illustrates active fixation of the preferred embodiment of the present inventive tined myocardial pacing lead to a myocardium. Utilizing a stylet, the lead assembly 10 is pressed against the epicardium and is rotated. The rough porous tip 9 abrades the epicardium and allows the tip 9 and the first row of tines 3 to penetrate the myocardium. The combination of pushing the tip electrode 9 toward the epicardium while rotating the electrode 9 at the same time results in only a gentle and significantly less force required to perforate the epicardium as compared to simply pushing the electrode 9 into the epicardium to achieve myocardial penetration. Excessive penetration into the myocardium is prevented by the second row of tines 7. The first row of tines 3 anchor on the inside wall of the epicardium thereby preventing accidental dislodgment without use of sufficient external force. Chronic fixation of the lead assembly 10 is achieved by "DACRON" pads 5 which adhere to the outside wall of the epicardium in as a result of fibrosis. Thus, controlling the depth of tip electrode 9 penetration into the myocardium, thereby ensuring the anchoring position of the first row of tines 3, further ensures that chronic removal of lead assembly 10 by counter traction can be accomplished without tearing or otherwise damaging the heart.

Figure 6:
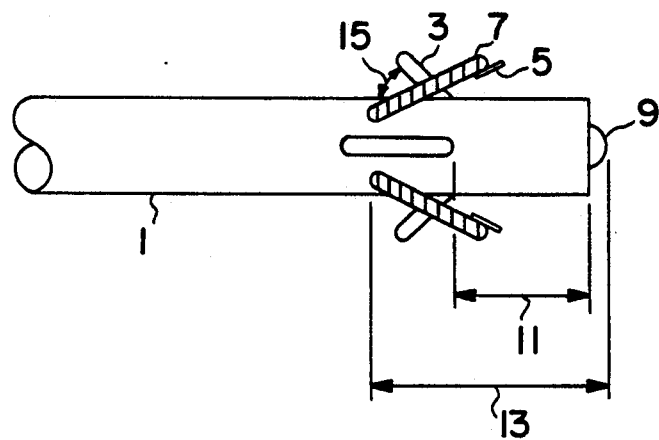
FIG. 6 illustrates another side view of the distal end portion of a preferred embodiment of the present invention depicting optimal dimensional criteria.

Moving now to FIG. 6, there is illustrated another side view of the preferred embodiment of the present inventive lead further depicting the angle 15 between the tines and lead body 1 as well as the distance 11 between the distal end of lead body 1 and the base of the first row of tines 3, and also the distance 13 between the distal most point of the electrode tip 9 and the base of the second row of tines 7. In the preferred embodiment, the tines (3,7), extend from the lead body 1 at an acute angle from 30° to less than 90° as described in U.S. Pat. No. 4,269,198 issued to Stokes and commonly assigned with the present invention to Medtronic, and incorporated herein by reference. However, in the preferred embodiment, the acute angle for both rows of tines (3,7) do not approach 90° simultaneously. At least one row of tines (3,7) will always have an acute angle substantially less than 90°.

In the preferred embodiment, the distance 11 between the distal end of lead body 1 and the base of the first row of tines 3 is equal to or less than about four millimeters. The distance 13 between the distal most point of electrode tip 9 and the base of the second row of tines 7, illustrated in FIG. 6 of the preferred embodiment must be sufficient to adequately penetrate the myocardium to a depth not exceeding 4 mm. Furthermore, the tip 9 must not perforate the endocardium. The angular and dimensional criteria hereinbefore described and illustrated in FIGS. 3–6 represent the preferred embodiment.

Figure 7:
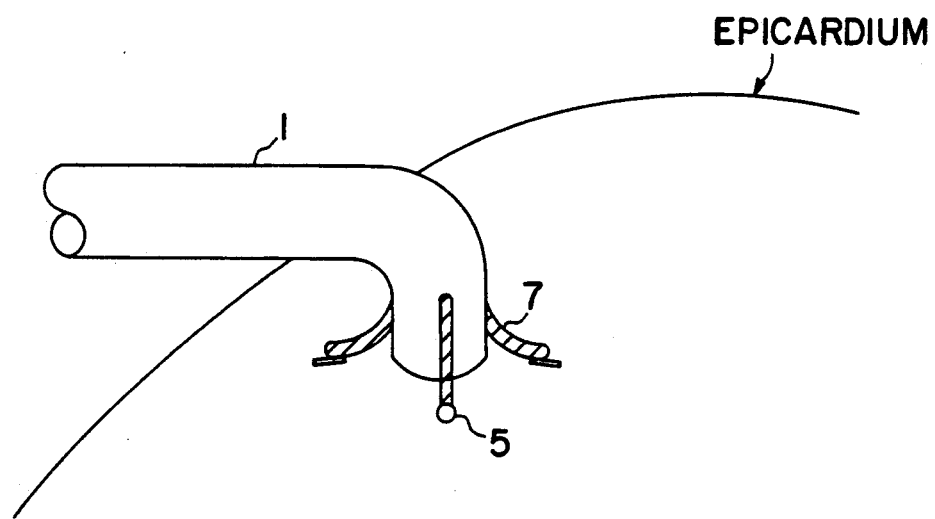
FIG. 7 illustrates a preferred embodiment of the present invention subsequent to active fixation to a myocardium and following removal of an insertion stylet, thereby allowing the preferred embodiment of the present invention to assume a stable preformed right angle shape.

FIG. 7 illustrates the preferred embodiment subsequent to implantation, further depicting active fixation of the present inventive lead assembly 10 following removal of the stylet used for guiding the lead assembly 10 into the myocardium. It can be seen that withdrawal of the stylet allows the preformed lead assembly 10 to assume its most stable right angle shape, thereby contributing to stabilization of the lead assembly 10 subsequent to implantation. Chronic removal is achieved by cutting the second row of tines 7 and then pulling the lead assembly 10 out by counter traction.

Obviously, many modifications and variations of the present invention are possible in light of the above teachings. For example, any body compatible material may be employed to form the exposed surface of the lead body and the tines, within the specified parameters. The number of tines may be varied according to preference and positioned around the periphery of a lead in accordance with known design considerations. The spacing between tine sets may be varied to address individual patient variations. In the illustrated embodiment, it is contemplated that four tines will be employed equidistantly positioned around the periphery of the lead. It is therefore to be understood that, within the scope of the appended claims, the invention may be practiced otherwise than as specifically described.

For example, a similar lead can be implanted transvenously to provide positive or passive fixation. Positive fixation in this case would be achieved by applying slight pressure and rotating the lead until the tip pops into the myocardium as for as the second row of tines will allow. Passive fixation would be achieved by simply placing the lead as any other tined lead. Thus, in one lead, one can achieve the implant characteristics of an epicardial lead, a transvenous tined lead and a transvenous active fixation lead.

What is claimed is:

1. A myocardial pacing lead comprising:
   an electrical conductor for supplying electrical stimulus to a patient's heart, said electrical conductor having a proximal end and a distal end;
   insulating sheath means for covering said conductor between said proximal and distal end of said conductor thereof;
   electrical connector means for electrically coupling said proximal end of said conductor to a pacemaker;
   electrode means electrically coupled to said distal end of said electrical conductor for conducting electrical energy to and from body tissue cells;
   first tine means extending from said insulating sheath means proximal said electrode means, said first tine means forming an acute angle with said proximal end of said conductor, said first tine means preventing dislodgement of said electrode means; and
   second tine means extending from said insulating sheath means proximal said first tine means and located between said first tine means and said proximal end of said conductor, said second tine means forming an acute angle with said distal end of said conductor, said second tine means preventing lead migration and excessive penetration of said electrode means.

2. The lead of claim 1 wherein said first tine means comprises a first plurality of pliable tines.

3. The lead of claim 2 wherein said first plurality of tines are spaced proximally equal to or less than about 4 millimeters from said distal end of said conductor.

4. The lead of claim 3 wherein said acute angle of said first tine means is from 30° to less than 90°.

5. The lead of claim 4 wherein said acute angle of said first tine means is from 30° to 80°.

6. The lead of claim 5 wherein said acute angle of said first tine means is from 45° to 60°.

7. The lead of claim 6 wherein said second tine means further comprises a synthetic fiber pad attached to a free floating end of each of said second tine means.

8. The lead of claim 5 wherein said second tine means further comprises a synthetic fiber pad attached to a free floating end of each of said second tine means.

9. The lead of claim 6 wherein said second tine means comprises a second plurality of pliable tines.

10. The lead of claim 9 wherein said acute angle of second tine means is 30° to 90°.

11. The lead of claim 10 wherein said acute angle of second tine means is 30° to 80°.

12. The lead of claim 9 wherein said second plurality of tines are spaced proximally less than about 20 millimeters from a distal end of said insulating sheath, said distal end of said insulating sheath means covering said distal end of said conductor.

13. The lead of claim 4 wherein said second tine means further comprises a synthetic fiber pad attached to a free floating end of each of said second tine means.

14. The lead of claim 4 wherein said second tine means comprises a second plurality of pliable tines.

15. The lead of claim 14 wherein said acute angle of second tine means is 30° to 80°.

16. The lead of claim 15 wherein said acute angle of said second tine means is 45° to 60°.

17. The lead of claim 14 wherein said second plurality of tines are spaced proximally less than about 20 millimeters from a distal end of said insulating sheath, said distal end of said insulating sheath means covering said distal end of said conductor.

18. The lead of claim 5 wherein said second tine means comprises a second plurality of pliable tines.

19. The lead of claim 18 wherein said acute angle of second tine means is 30° to 90°.

20. The lead of claim 18 wherein said second plurality of tines are spaced proximally less than about 20 millimeters from a distal end of said insulating sheath, said distal end of said insulating sheath means covering said distal end of said conductor.

21. A method of implanting a cardiac pacing lead comprising:
    selecting a pacing lead of the type comprising a proximal end and a distal end having an electrode extending therefrom, a first plurality of radially extending tines proximal said electrode, and a second plurality of radially extending tines located between said first plurality of tines and said proximal end of said lead, said second plurality of tines having a synthetic fiber pad attached to a free floating end of each of said tines;
    inserting said electrode and said first and second plurality of radially extending tines into the myocardium of a patient's heart until said first and second plurality of radially extending tines have completely entered the myocardium of said patient's heart; and
    withdrawing said lead slightly from said patient's heart such that said first plurality of radially extending tines expands radially within the tissue of said patient's heart, adjacent an inner surface of the myocardium of said patient's heart, and such that said second plurality of radially extending tines expands radially, adjacent an outer surface of the epicardium of said patient's heart whereby said synthetic fiber pads adhere to said outer surface of said epicardium.

* * * * *